United States Patent [19]

Hoelderich et al.

[11] Patent Number: 5,144,061
[45] Date of Patent: Sep. 1, 1992

[54] PREPARATION OF ALKENECARBOXYLIC ESTERS

[75] Inventors: Wolfgang Hoelderich, Frankenthal; Fritz Naeumann, Mannheim; Rolf Fischer, Heidelberg, all of Fed. Rep. of Germany

[73] Assignee: BASF Aktiengesellschaft, Ludwigshafen, Fed. Rep. of Germany

[21] Appl. No.: 116,865

[22] Filed: Nov. 5, 1987

[30] Foreign Application Priority Data

Nov. 7, 1986 [DE] Fed. Rep. of Germany ....... 3638010

[51] Int. Cl.$^5$ ............................................. C07C 67/30
[52] U.S. Cl. ................................................. 560/212
[58] Field of Search .............. 560/212, 214, 217, 130

[56] References Cited

U.S. PATENT DOCUMENTS

| | | | |
|---|---|---|---|
| 2,376,704 | 5/1945 | Kung | 560/212 |
| 4,085,275 | 4/1978 | Gambell et al. | 560/217 X |
| 4,777,285 | 10/1988 | Kummer et al. | 560/205 |
| 4,788,326 | 11/1988 | Hoelderich et al. | 560/205 |

FOREIGN PATENT DOCUMENTS

| | | |
|---|---|---|
| 0206143 | 12/1986 | European Pat. Off. |
| 0238002 | 9/1987 | European Pat. Off. |
| 12125 | 5/1968 | Japan ................... 560/212 |
| 668285 | 3/1952 | United Kingdom .......... 560/212 |

*Primary Examiner*—Arthur C. Prescott
*Assistant Examiner*—V. Garner
*Attorney, Agent, or Firm*—Keil & Weinkauf

[57] ABSTRACT

The present invention relates to a method for producing optically active alcohol derivatives, which are useful as fungicides, herbicides or plant growth regulators, represented by the formula,

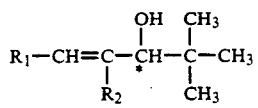

by carrying out the asymmetric reduction of a ketone compound represented by the formula,

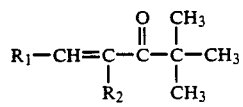

with a boron hydride-reducing agent modified with an optically active amino alcohol represented by the formula,

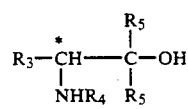

and also relates to the boron hydride type compound obtained by reacting the above optically active amino alcohol with a boron hydride compound and its production method.

10 Claims, No Drawings

PREPARATION OF ALKENECARBOXYLIC ESTERS

The present invention relates to a process for preparing an alkenecarboxylic ester by reacting a lactone with an alcohol in the presence of a catalyst.

Nippon Nogei Kogaku Kaishi 48 (1974), pages 525–527 and C.A. 82 (1975), 124.673 disclose that omega-hydroxycarboxylic esters are obtainable by reacting 5-, 6- or 7-membered lactones with alcohols in the presence of magnesium alcoholates or acids.

It has also been disclosed that 3-pentenic esters are isomerized to 4-pentenic esters at from 100° to 150° C. in the presence of acid ion exchangers or acid zeolites which contain noble metals of group VIII of the periodic table, such as palladium, rhodium or ruthenium (German Laid-Open Application DOS 3,317,163). For instance, starting from mixed methyl 3-pentenate isomers (70% trans, 30% cis) which contain 8% by weight of the desired methyl 4-pentenate ester, as well as unconverted methyl 3-pentenate and small amounts of 2-pentenic esters. The 4-pentenic ester can be separated from such mixtures of isomers by azeotropic distillation with water (German Laid-Open Application DOS 3,412,295). The disadvantage with this procedure is that the 4-pentenic ester content of the isomeric mixtures is not increasable substantially over 8% by weight. As a consequence, separating off the 4-pentenic ester and recycling the 2- and 3-pentenic esters make for expensive distillation.

It is an object of the present invention to provide a single-stage process for preparing an alkene carboxylic ester having a terminal double bond starting from a corresponding 5-, 6- or 7-membered lactone.

It is a further object of the present invention to develop a process giving a higher 4-pentenic ester content in the mixture of pentenic ester isomers.

We have found that these objects are achieved in a process for preparing an alkenecarboxylic ester of the formula I

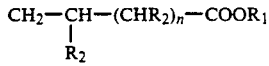

where $R_1$ is alkyl of 1 to 6 carbon atoms, $R_2$ is hydrogen or alkyl of 1 to 4 carbon atoms, the substituents being identical or different, and n is 1, 2 or 3, by reacting a lactone of the formula II

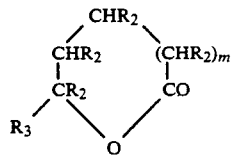

where $R_2$ has the same meanings as in the formula I, $R_3$ is hydrogen or methyl and m is 0, 1 or 2, with the to a proviso that n and m differ by 1 when $R_3$ is hydrogen and by 2 when $R_3$ is methyl, with an alkanol of 1 to 6 carbon atoms at from 50° to 450° C. in the presence of a catalyst, the catalyst used being a zeolite and/or a phosphate.

We have found it to be particularly advantageous to operate in the gas phase at from 100° to 450° C.

The novel process has the advantage of producing an alkenecarboxylic ester having a terminal double bond from a 5-, 6- or 7-membered lactone in good yield in a single stage. The novel process has the further advantage of being simple to carry out in industry and of producing better yields of 4-pentenic esters on using 5-methylbutyrolactone.

The novel process is remarkable since the lactone cleavage to an alkenecarboxylic ester takes place preferentially compared with the similarly acid-catalyzed ether formation from the alcohols involved.

Similarly, the formation of a pentenic ester, in particular a 4-pentenic ester, in the reaction of 5-methylbutyrolactone with an alcohol in the presence of a zeolite and/or phosphate as catalyst is surprising and has hitherto not been described.

Nor was it foreseeable that cleaving 5-methylbutyrolactone with an alcohol in the presence of a zeolite and/or phosphate as catalyst would produce 4-pentenic esters in high yields, as well as cis- and trans-3-pentenic esters, and would substantially suppress, if not completely avoid, the formation of 2-pentenic esters. The reason this is of special significance is that, for example, methyl 2-cis-pentenate cannot be separated from methyl 4-pentenate by distillation because the boiling point is the same (129° C.).

According to the invention, the starting point is a lactone of the formula II. Suitable lactones are for example caprolactone, 7-methylcaprolactone, delta-valerolactone, 6-methylvalerolactone, butyrolactone and 5-methylbutyrolactone. Preferred starting materials are caprolactone, delta-valerolactone and 5-methylbutyrolactone.

The reaction is carried out with an alkanol of 1 to 6 carbon atoms. Suitable alkanols are for example methanol, ethanol, propanol, butanol, isopropanol, isobutanol, secondary butanols, n-pentanol and n-hexanol. Methanol, ethanol and propanols are particularly suitable.

The reaction according to the invention can be illustrated, for example for the case of methyl 4-pentenate, by the following equation:

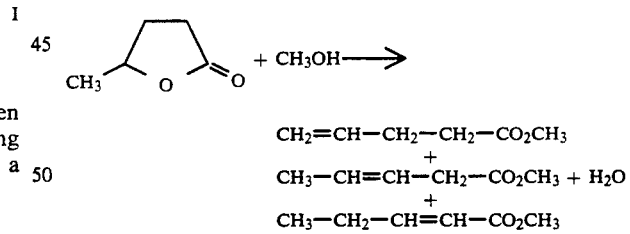

Other products in addition to methyl 4-pentenate are methyl 3-pentenate and methyl 2-pentenate which, with the exception of methyl 2-cis-pentenate (which is only present in a small amount), can be separated from methyl 4-pentenate by distillation.

The catalyst used for the process according to the invention is an acidic zeolitic catalyst. Zeolites are for example crystalline aluminosilicates which have a highly ordered structure comprising a rigid three-dimensional network of $SiO_4$ and $AlO_4$ tetrahedra linked by a common oxygen atom. The ratio of the Si and Al atoms oxygen is 1:2 (see Ullmann's Encyclopädie d. techn: Chemie, 4th edition, volume 24, page 575 (1983)). The electrovalence of the aluminum-containing tetrahedra is balanced by the inclusion in the crystal of cations, for example an alkali metal or hydrogen ion. Cation exchange is possible. The spaces between the tetrahedra are occupied by water molecules prior to dehydration through drying or calcination.

In the zeolites, the aluminum in the lattice can be replaced by other elements such as B, Ga, Fe, Cr, V, As, Sb, Bi or Be or mixtures thereof, or the silicon can be replaced by a tetravalent element such as Ge, Ti, Zr, or Hf.

According to their structure, zeolites are divided into various groups (see Ullmann's Encycopädie d. techn. Chemie, 4th edition, volume 24, page 575 91983)). For instance, the zeolite structure in the mordenite group is formed by tetrahedra arranged in chains and in the chabisite group by tetrahedra arranged in layers, while in the faujasite group the tetrahedra form polyhedra, for example in the form of a cuboctahedron which is composed of tetragons and hexagons. Depending on the way the cuboctahedra linked, which produces differently sized voids and pores, zeolites are classed as type A, L, X or Y.

Catalysts suitable for the process according to the invention are preferably zeolites from the mordenite group or narrow-pored zeolites of the erionite or chabasite type or zeolites of the faujasite type, for example Y-, X- or L-zeolites. This group of zeolites also includes the ultrastable zeolites of the faujasite type, i.e. dealuminized zeolites. Methods for preparing such zeolites are described in Catalysis by Zeolites, volume 5 of Studies in Surface Science and Catalysis, ed. B. Imelik et al., Elsevier Scientific Publishing Comp. 1980, page 203 and Crystal Structures of Ultra-stable Faujasites, Advances in Chemistry Series No. 101, American Chemical Society Washington D.C., pages 226 et seq. (1971) and in U.S. Pat. No. 4,512,961.

Zeolites of the pentasil type are particularly advantageous. Their common feature is a pentagon composed of $SiO_4$ tetrahedra. They are characterized by a high $SiO_2/Al_2O_3$ ratio and by pore sizes between those of the zeolites of type A and those of type X or Y (cf. Ullmann's Encyclopadie d. techn. Chem., 4th edition, volume 24, page 575, 1983).

These zeolites can have different chemical compositions. They can be aluminosilicate, borosilicate or iron, beryllium, gallium, chromium, arsenic, antimony or bismuth silicate zeolites or mixtures thereof, aluminogerminate, borogerminate and gallium or iron germinate zeolites or mixtures thereof. Particularly suitable for the process according to the invention are the aluminosilicate, borosilicate and iron silicate zeolites of the pentasil type. The aluminosilicate zeolite is prepared for example from an aluminum compound, preferably Al(OH)$_3$ or Al$_2$(SO$_4$)$_3$, and a silicon component, preferably finely divided silicon dixoide, in an aqueous amine solution, in particular in polyamines such as 1,6-hexanediamine or 1,3-propanedia-mine or triethylenetetramine solution, in the presence or in particular in the absence of alkali metal or alka-line earth metal at from 100° to 220° C. under autogenous pressure. This also includes the isotactic zeolites described in German Laid-Open Application DOS 3,006,471. The aluminosilicate zeolites obtained have an $SiO_2/Al_2O_3$ ratio of from 10 to 40,000, depending on the mixing ratio of the starting materials. These aluminosilicate zeolites can also be synthesized in an ether medium such as diethylene glycol dimethyl ether, in an alcohol medium such as methanol or 1,4-butanediol or in water.

The borosilicate zeolite is synthesized for example at from 90° to 200° C. under autogenous pressure by reacting a boron compound, for example H$_3$BO$_3$, with a silicon compound, preferably finely divided silicon dioxide in an aqueous amine solution, in particular in 1,6-hexanediamine or 1,3-propanediamine or triethylenetetramine solution, in the presence or in particular in the absence of alkali metal or alkaline earth metal. They also include the isotactic zeolites described in German Laid-Open Application DOS 3,006,471 and EP 46,504. These borosilicate zeolites can also be prepared by carrying out the reaction not in aqueous amine solution but in an ether solution, for example diethylene glycol dimethyl ether, or in an alcoholic solution, for example 1,6-hexanediol.

The iron silicate zeolite is obtained for example from an iron compound, preferably Fe$_2$(SO$_4$)$_3$, and a silicon compound, preferably finely divided silicon dioxide in an aqueous amine solution, in particular 1,6-hexanediamine, in the presence or absence of alkali metal or alkaline earth metal at from 100° to 220° C. under autogenous pressure.

The high-silicon zeolites ($SiO_2/Al_2O_3 \geq 10$) which can be used also include the ZSM types, for example ZSM 5, a crystalline aluminosilicate zeolite disclosed in U.S. Pat. No. 3,702,886. The preparation is described for example in Examples 1, 2, 6, 22, 26 and 27 of U.S. Pat. No. 3,702,886.

ZSM 8, a crystalline aluminosilicate zeolite protected in U.S. Pat. No. 3,709,979. Its preparation is described in Examples 1, 2, 4, 5, 8 and 10.

ZSM 12, a crystalline aluminosilicate zeolite disclosed in U.S. Pat. No. 3,832,449 and prepared as described in Examples 1 to 8.

ZSM 21, a crystalline zeolite disclosed in U.S. Pat. No. 4,046,859.

ZSM 22, a crystalline zeolite disclosed in EP 102,716.

ZSM 23, a crystalline zeolite disclosed in U.S. Pat. No. 4,076,842.

ZSM 25, a crystalline zeolite described in U.S. Pat. No. 4,247,416.

ZSM 34, a crystalline aluminosilicate zeolite disclosed in U.S. Pat. No. 4,086,186.

ZSM 35, a crystalline zeolite disclosed in U.S. Pat. Nos. 4,016,245 and 4,107,195.

ZSM 48, a crystalline zeolite disclosed in U.S. Pat. No. 4,448,675.

Ferrierite, a crystalline zeolite disclosed in EP 12,473.

NU-1, a crystalline zeolite disclosed in U.S. Pat. No. 4,060,590.

Silicalite ®, a silica polymorph molecular sieve disclosed in detail in U.S. Pat. No. 4,061,724.

The aluminosilicate, borosilicate and iron silicate zeolites thus prepared, after they have been isolated, dried at from 100° to 160° C., preferably at 110° C., and calcined at from 450° to 550° C., preferably at 500° C., can be combined with a binder in a ratio of from 90:10 to 40:60, % by weight, and molded into extrudates or tablets. Suitable binders are various aluminum oxides, preferably boehmite, amorphous alumina silicates having an $SiO_2/Al_2O_3$ ratio of from 25:75 to 90:5, preferably 75:25, silicon dioxide, preferably finely divided SiO$_2$, mixtures of finely divided SiO$_2$ and finely divided Al$_2$O$_3$, TiO$_2$, ZrO$_2$, and clay. After molding, the extrudates or tablets are for example dried at 110° C./16 h and calcined at 500° C./16 h.

It is also possible to obtain advantageous catalysts by molding the isolated aluminosilicate or borosilicate zeolite immediately after drying and subjecting it to calcination only after molding. The aluminosilicate and borosilicate zeolites prepared can be used in the pure form, without binder, as extrudates or tablets, the extrusion or peptization aids used being for example ethylcellulose, stearic acid, potato starch, formic acid, oxalic acid, acetic acid, nitric acid, ammonia, amines, silica esters and graphite or mixtures thereof.

If the zeolite, on account of its manner of preparation, is not present in the catalytically active, acidic H-form but is, for example, in the Na-form, it can be completely or partially converted into the desired H-form by ion exchange, for example with ammonia ions, and subsequent calcination, or by treatment with acids.

Should the zeolite catalyst used according to the invention undergo deactivation due to coking, it is advisable to regenerate the zeolite by burning off the coke deposit with air or with an air/$N_2$ mixture at from 400° to 550° C. This restores the initial activity level of the zeolite.

By precoking it is possible to set the activity of the catalyst for optimum selectivity of the desired reaction product.

To obtain a high selectivity, high conversion and long times on stream, it is advantageous to modify the zeolites. A suitable method of modifying the catalyst comprises for example doping the shaped or unshaped zeolite with metal salts by ion exchange or impregnation. The metals used are alkali metals such as Li, Cs or K, alkali earth metals such as Mg, Ca, or Sr, metals of main groups III, IV and V, such as Al, Ga, Ge, Sn, Pb or Bi, transition metals of subgroups IV-VIII, such as Ti, Zr, V, Nb, Cr, Mo, W, Mn, Re, Fe, Ru, Os, Co, Rh, Ir, Ni, Pd, Pt, transition metals of subgroups I and II, such as Cu, Ag or Zn, and rare earth metals such as La, Ce, Pr, Nd, Fr, Yb and U. Advantageously, the metals mentioned are present in from 0.1 to 3% by weight, calculated as metal.

For example, doping is carried out advantageously by introducing the molded zeolite into a riser pipe and passing an aqueous or ammoniacal solution of a halide or nitrate of one of the abovementioned metals over it at from 20° to 100° C. Such an ion exchange can take place for example with the hydrogen, ammonium or alkali metal form of the zeolite. Another way of applying metal to the zeolite comprises impregnating the zeolitic material with, for example, a halide, nitrate or oxide of one of the abovementioned metals in aqueous, alcoholic or ammoniacal solution. Both ion exchange and impregnation are followed by at least a drying step, optionally by repeated calcination.

A possible embodiment comprises for example dissolving $Cu(NO_3)_2 \times 3H_2O$ or $Ni(NO_3)_2 \times 6H_2$ or $Ce(NO_3)_3 \times 6H_2O$ or $La(NO_3)_2 \times 6H_2O$ or $Cs_2CO_3$ in water and impregnating the molded or unmolded zeolite with this solution for a certain period, for example 30 minutes. Any supernatant liquor is stripped of water in a rotary evaporator. The impregnated zeolite is then dried at about 150° C. and calcined at about 550° C. This impregnating step can be carried out several times in succession until the desired metal content is obtained.

It is also possible to prepare for example an aqueous $Ni(NO_3)_2$ solution or ammoniacal $Pd(NO_3)_2$ solution and to suspend the pure pulverulent zeolite therein at from 40° to 100° C. by stirring for about 24 hours. After filtration, drying at about 150° C. and calcination at about 500° C., the zeolitic material thus obtained can be further processed with or without binders into extrudates, pellets or fluidizable material.

An ion exchange on the zeolite present in the H-form or ammonium form or alkali metal form can be carried out by introducing the zeolite in extruded or pellet form into a column and for example passing an aqueous $Ni(NO_3)_2$ solution or ammoniacal $Pd(NO_3)_2$ solution over it in a recycle loop and at a slightly elevated temperature of from 30° to 80° C. for from 15 to 20 hours. This is followed by washing with water, drying at about 150° C. and calcination at about 550° C. With some metal-doped zeolites, for example Pd-, Cu- or Ni-doped zeolites, an aftertreatment with hydrogen is advantageous.

A further method of modifying the zeolite comprises treating the zeolitic material, which may be in molded or unmolded form, with an acid such as hydrochloric acid, hydrofluoric acid or phosphoric acid and/or steam, advantageously, for example, by treating the zeolite in pulverulent form with 1N phosphoric acid at 80° C. for 1 hour and then washing with water, drying at 110° C./16 hours and calcining at 500° C./20 hours. Alternatively, before or after being molded together with a binder, the zeolite is treated for example at from 60° to 80° C. with from 3 to 25% strength by weight, in particular from 12 to 20% strength by weight, aqueous hydrochloric acid for from 1 to 3 hours. Afterwards, the zeolite thus treated is washed with water, dried and calcined at from 400° C. to 500° C.

A particular embodiment of the acid treatment comprises treating the zeolitic material, before it is molded, with hydrofluoric acid, generally in the form of 0.001N to 2N, preferably 0.05N to 0.5N, hydrofluoric acid, at an elevated temperature, for example by heating under reflux for, in general, from 0.5 to 5, preferably from 1 to 3, hours. After the zeolitic material has been isolated, for example by filtering and washing, it is advantageously dried, for example at from 100° to 160° C., and calcined, in general at from 450° C. to 600° C. In a further preferred form of the acid treatment, the zeolitic material, after it has been molded together with a binder, is treated at an elevated temperature, advantageously at from 50° C. to 90° C., preferably at from 60° C. to 80° C., for from 0.5 to 5 hours with, preferably, from 12 to 20% strength by weight hydrochloric acid. The zeolitic material is in general subsequently washed, expediently dried at from 100° to 160° C. and calcined at, in general, from 450° to 600° C. An HF treatment can also be followed by an HCl treatment.

Another possibility is to modify zeolites by applying phosphorus compounds, such as trimethoxy phosphate, trimethoxy phosphine, or primary, secondary or tertiary sodium phosphate. The treatment with primary sodium phosphate has proven particularly advantageous. It comprises treating the zeolite in extrudate, tablet or fluidizable form with aqueous $NaH_2PO_4$ solution, drying at 110° C. and calcining at 500° C.

Further catalysts for preparing an alkenecarboxylic ester from a lactone are phosphates, in particular aluminum phosphates, silicon aluminum phosphates, silicon iron aluminum phosphates, iron aluminum phosphate, cerium phosphate, strontium phosphate zirconium phosphate, boron phosphate, iron phosphate and mixtures thereof. Hydrothermally prepared phosphates are advantageous.

Aluminum phosphate catalysts used for the process according to the invention are in particular aluminum phosphates synthesized under hydrothermal conditions.

Aluminum phosphates prepared under hydrothermal conditions are for example APO-5, APO-9, APO-12, APO-14, APO-21, APO-25, APO-31 and APO-33. Syntheses of these compounds are described in EP 132,708, U.S. Pat. No. 4,310,440 and U.S. Pat. No. 4,473,663.

AlPO$_4$-5 (APO-5), for example, is synthesized by homogeneously mixing orthophosphoric acid with pseudoboehmite in water, adding tetrapropylammonium hydroxide to this mixture and then reacting at about 150° C. under autogeneous pressure in an autoclave for from 20 to 60 hours. The AlPO$_4$ is filtered off, dried at from 100° to 160° C. and calcined at from 450° to 550° C.

AlPO$_4$-9 (APO-9) is likewise synthesized from orthophosphoric acid and pseudoboehmite, but in an aqueous DABCO solution (1,4-diazabicyclo-(2,2,2)-ocatane) at about 200° C. under autogenous pressure in from 200 to 400 hours.

AlPO$_4$-21 (APO-21) is synthesized from orthophosphoric acid and pseudoboehmite in an aqueous pyrrolidine solution at from 150° to 200° C. under autogeneous pressure in the course of from 50 to 200 hours.

The silicon aluminum phosphates used for the process according to the invention are for example SAPO-5, SAPO-11, SAPO-31 and SAPO-34. The synthesis of this type of compound is described for example in EP 103,117 and U.S. Pat. No. 4,440,871. SAPOs are prepared by crystallization from an aqueous mixture at from 100° to 250° C. under autogenous pressure in the course of from 2 hours to 2 weeks, during which the reaction mixture, comprising a silicon, an aluminum and a phosphorus component, is converted in an aqueous aminoorganic solution.

SAPO-5 is obtained for example by mixing SiO$_2$ suspended in aqueous tetrapropylammonium hydroxide solution with an aqueous suspension of pseudoboehmite and orthophosphoric acid and subsequently reacting at from 150° to 200° C. under hydrogenous pressure in a stirred autoclave for from 20 to 200 hours. The powder is filtered off, dried at from 110° to 160° C. and calcined at from 450° to 550° C.

Si-AlPO$_4$-11 (SAPO-11) is for example synthesized from a mixture of 200 g of H$_3$PO$_4$, 136 g of AlOOH, 60 g of 30% strength silica sol, 91 g of dipropylamine and 890 g of water. The reaction is carried out under hydrogenous pressure at 200° C. for 96 hours. Filtration is followed by drying at 120° C. and calcination at 500° C.

Suitable silicon aluminum phosphates are for example ZYT-5, ZYT-6, ZYT-7, ZYT-9, ZYT-11 and ZYT-12 (J 5 9217-619).

The phosphate catalysts used for the process according to the invention also include precipitated aluminum phosphates. Such an aluminum phosphate is prepared for example by dissolving 92 g of diammonium hydrogenphosphate in 700 ml of water, and adding to this solution 260 g of Al(NO$_3$)$_3\times$H$_2$O in 700 ml of water in the course of 2 hours, during which pH 8 is maintained by simultaneously adding 25% strength NH$_3$ solution. The resulting precipitate is subsequently stirred for 12 hours, then filtered off under suction and washed. It is dried at 60° C./6 h.

Boron phosphates for the process according to the invention can be prepared for example by mixing and kneading concentrated boric acid and phosphoric acid and by subsequent drying and calcination in an inert gas, air or steam atmosphere at from 250° to 650° C., preferably from 300° to 500° C.

The catalyst described herein can optionally be used in the form of from 2 to 4 mm extrudates or as tablets from 3 to 5 mm in diameter or as chips from 0.1 to 0.5 mm in particle size, or in a fluidizable form.

The process according to the invention is in general carried out under the following reaction conditions:

The molar ratio of lactone of the formula II:

The molar ratio of lactone of the formula II:alkanol advantageously ranges from 1:0.5 to 1:10, in particular from 1:1 to 5.

In the reaction, a temperature of from 50° to 450° C. is maintained. The reaction is carried out in particular in the gas phase at from 100° to 450° C. Advantageously, a temperature of from 150° to 400° C., in particular from 200° to 350° C., is maintained. In general, the reaction is carried out under a pressure of from 0.1 to 100 bar, in particular from 0.5 to 10 bar.

If the lactone of the formula II is converted in the gas phase over one of the catalysts described above, the weight hourly space velocity through the catalyst (WHSV = g of feed mixture/g of catalyst/hour) is advantageously maintained within the range from 0.1 to 20, in particular from 1 to 10, g of lactone of the formula II per g of catalyst per hour.

The reaction in the gas phase can be carried out in a fixed bed or in a fluidized bed.

It is also possible to carry out the reaction in the liquid phase, for example in a suspension, trickle bed or liquid phase procedure, at from 50° to 200° C.

The reaction can be carried out batchwise, but is preferably carried out continuously.

Involatile or solid starting materials are used in dissolved form, for example in tetrahydrofuran, toluene or petroleum ether solution. In general, the starting material can be diluted with such a solvent or with an inert gas such as N$_2$, Ar or steam.

After the reaction the resulting products are isolated from the reaction mixture in a conventional manner, for example by distillation; unconverted starting mixture may be recycled if necessary into the reaction according to the invention.

The omega-alkenecarboxylic esters obtainable by the process according to the invention are versatile intermediates, for example for preparing alpha, omega-dicarboxylic acids.

The process according to the invention is suitable in particular for preparing 4-pentenic esters and has the advantage compared with the isomerization of 3-pentenic esters to 4-pentenic esters that higher 4-pentenic ester contents are obtained in the mixture of pentenic ester isomers. This makes it easier to separate off the 4-pentenic esters. 2- and 3-pentenic esters can be converted back into 5-methylbutyrolactone, after hydrolysis to the corresponding pentenic acids, in the presence of sulfuric acid as catalyst (R. P. Linstead, J. Chem. Soc. 1932, pages 115–129).

The 4-pentenic esters obtainable by the process according to the invention are useful intermediates which are convertible into 5-formylvaleric esters by low-pressure hydroformylation in the presence of Rh compounds as catalysts (German Laid-Open Application DOS 3,317,164). 5-formylvaleric esters can be converted to caprolactam by aminating hydrogenation and cyclization of the corresponding aminocaproic esters without production of ammonium sulfate.

The process according to the invention is illustrated by the following Examples.

EXAMPLES 1 TO 13

5-methylbutyrolactone and methanol in the molar ratio of 1:3 were vaporized and reacted in the gas phase under isothermal conditions in a tubular reactor (helix, internal diameter 0.6 cm, length 90 cm) packed with a catalyst in the course of 6 hours. The reaction products were condensed, separated off and characterized. The quantitative determination of the reaction products and of the starting materials was carried out by gas chromatography. The temperatures, catalysts and mixing ratios employed and the results obtained can be seen in Table 1.

The catalysts used for the process according to the invention are:

Catalyst A

A borosilicate zeolite of the pentasil type is prepared in a hydrothermal synthesis from 640 g of finely divided $SiO_2$, 122 g of $H_3BO_3$, and 8,000 g of an aqueous 1,6-hexanediamine solution (mixture 50:50% by weight) at 170° C. under autogenous pressure in a stirred autoclave. After filtering and washing, the crystalline reaction product is dried at 100° C./24 h and calcined at 500° C./24 h. This borosilicate zeolite comprises 94.2% by weight of $SiO_2$ and 2.3% by weight of $B_2O_3$.

This material is molded with a molding aid into 2-mm extrudates which are dried at 110° C./16 h and calcined at 500° C./24 h.

Catalyst B

An aluminosilicate zeolite of the pentasil type is prepared under hydrothermal conditions at autogenous pressure and 150° C. from 65 g of finely divided $SiO_2$, 20.3 g of $Al_2(SO_4)_3 \times 18H_2O$ in 1 kg of an aqueous 1,6-hexanediamine solution (50:50% by weight) in a stirred autoclave. After filtering and washing, the crystalline reaction product is dried at 110° C./24 h and calcined at 500° C./24 h. This aluminosilicate zeolite contains 91.6% by weight of $SiO_2$ and 4.6% by weight of $Al_2O_3$. The catalyst is molded into 2-mm extrudates, dried at 110° C./16 h and calcined at 500° C./24 h.

Catalyst C

Commercial Na-Y zeolite is ion exchanged with aqueous $(NH_4)_2SO_4$ solution in a conventional manner until the Na content is less than 0.05% by weight (after drying at 110° C./2 h and calcination at 570° C./3 h). The powder thus obtained is molded with molding aids into extrudates, dried at 110° C. and calcined at 500° C./16 h.

Catalyst D $AlPO_4$-9 (APO-9) is synthesized by dissolving or suspending 200 g of 98% pure phosphoric acid and 136 g of boehmite in 400 g of water, adding an aqueous solution of 112 g of diazobicyclo-2,2,2-octane (DABCO) and 320 g of $H_2O$, and reacting this mixture at 200° C. in a stirred autoclave under autogenous pressure for 336 hours. After filtering, the crystalline material is dried at 120° C. and calcined at 500° C./16 h. The $AlPO_4$-9 thus synthesized contains 49.0% by weight of $P_2O_5$ and 37.1% by weight of $Al_2O_3$. This material is molded with finely divided $SiO_2$ in a weight ratio of 80:20 into 3-mm extrudates, dried once more at 120° C. and calcined at 500° C./6 h.

Catalyst E $SiAlPO_4$-5 (SAPO-5) is prepared from a mixture of 200 g of 98% pure phosphoric acid, 136 g of boehmite, 60 g of 30% strength silica sol, 287 g of tripropylamine and 587 g of $H_2O$. This mixture is reacted at 150° C. under autogenous pressure for 168 hours. After filtration the crystalline product is dried at 120° C. and calcined at 500° C. SAPO-5 contains 49.8% by weight of $P_2O_5$, 33.0% by weight of $Al_2O_3$, and 6.2% by weight of $SiO_2$. SAPO-5 is molded with an extruding aid into 3-mm extrudates, dried at 120° C. and calcined at 500° C.

Catalyst F

Catalyst F is obtained by ion exchanging catalyst A with 20% strength aqueous $LiNO_3$ solution at 80° C./2 h. This is followed by washing with $H_2O$, drying at 110° C. and calcining at 500° C./5 h. The Li quantity is 0.24% by weight.

Catalyst G $BPO_4$ is prepared by adding 49 g of $H_3BO_3$ together with 117 g of 75% strength $H_3PO_4$ together in a kneader, evaporating off excess water and molding the reaction product into 3-mm extrudates. These extrudates are dried at 100° C. and calcined at 350° C. Catalyst G contains 8.77% by weight of B and 28.3% by weight of P.

Catalyst H $CePO_4$ is obtained by precipitation from 52 g of $Ce(NO_3)_3 \times 6H_2O$ and 56 g of $NaH_2PO_4 \times 2H_2O$. After filtration, the material is molded into extrudates, dried at 120° C. and calcined at 450° C. Catalyst H contains 47.1% by weight of Ce and 12.7% by weight of P.

Catalyst I

Commercial $Zr_3(PO_4)_4$ is molded with molding aids into 2-mm extrudates, dried at 110° C. and calcined at 500° C./16 h.

Catalyst J (Comparative catalyst)

$Al_2O_3$ catalyst

Catalyst K (Comparative catalyst)

$SiO_2$ catalyst

The experimental results are summarized in Table 1 together with data about reaction conditions.

The comparative examples involving comparative catalyst K and L show that, in total, the conversions and selectivities for methyl 3- and 4-pentenates are lower than in the process according to the invention and that more methyl 2-pentenate is formed (=total pentenate minus 4-pentenat minus 3-pentenate).

EXAMPLE 14

5-methylbutyrolactone was reacted with $CH_3OH$ (1:3 molar ratio) over catalyst A at 220° C. using a WHSV of 1.6 $h^{-1}$. During a run of 160 h the 4-pentenate content (4-PSE) showed no significant change (Table 2).

TABLE 2

| | Time h | | | | |
| --- | --- | --- | --- | --- | --- |
| | 6 h | 46 h | 94 h | 138 h | 154 h |
| 4-PSE % by volume | 19.9 | 19.8 | 20.2 | 19.4 | 20.8 |

EXAMPLE 15

A mixture of delta-valerolactone and methanol (1:3 molar ratio) was reacted over catalyst A at 300° C. using a WHSV of 1.5 $h^{-1}$ in the apparatus described above. The conversion was 99.1%, while the selectivities obtained were 12% for 4-pentenate, 48.0% for 3-pentenate, 19.5% for 2-pentenate and 14.4% for 5-methylbutyrolactone. Since 5-methylbutyrolactone can likewise be converted into pentenate the total selectivity for pentenate can be increased to about 94%.

EXAMPLE 16

A mixture of caprolactone and methanol (1:3 molar ratio) was reacted over a catalyst A at 300° C. using a WHSV-1.8 $h^{-1}$ in the apparatus described above. The conversion was 98.6% and the selectivity for methyl hexenate 88.8%.

EXAMPLE 17

A V4A stainless steel reactor 2.4 cm in internal diameter and 49 cm in length thermostated in a salt bath was charged with 50 g of catalyst A. Under isothermal conditions a mixture of caprolactone and methanol (molar ratio 1:3) was reacted. The temperature was varied within the range from 300° to 350° C. The WHSV was 41 g of mixture per hour. Furthermore, 30 liters of $N_2$/h were passed in as purge gas. The yield of methyl hexenate ranged from 80 to 78.7% during a 14-day run.

TABLE 1

Reaction of 5-methylbutyrolactone with methanol (1:3 molar) to methyl pentenate

| Example | 1 | 2 | 3 | 4 | 5 | 6 | 7 | 8 | 9 | 10 | 11* | 12* |
|---|---|---|---|---|---|---|---|---|---|---|---|---|
| Catalyst | A | A | B | C | D | E | F | G | H | I | J* | K* |
| Temperature | 220° C. | 300° C. | 300° C. | 250° C. | 300° C. | 300° C. | 300° C. | 300° C. | 300° C. | 300° C. | 220° C. | 300° C. |
| WHSV [$h^{-1}$] | 1.5 | 10 | 6 | 1.5 | 1.5 | 1.5 | 1.5 | 1.5 | 1.5 | 1.5 | 1.5 | 1.5 |
| Conversion % | 65.1 | 66.9 | 67.0 | 60.6 | 72.2 | 59.1 | 13.0 | 29.4 | 30.2 | 29.5 | 16.0 | 35.4 |
| Selectivity % | | | | | | | | | | | | |
| 4-PSE | 29.2 | 33.4 | 16.5 | 24.7 | 29.2 | 35.0 | 47.6 | 38.3 | 32.5 | 34.2 | 22.3 | 35.5 |
| 3-PSE | 67.0 | 61.4 | 71.9 | 69.6 | 40.9 | 38.1 | 21.5 | 38.4 | 41.1 | 37.3 | 21.9 | 44.1 |
| PSE | 96.9 | 97.8 | 98.1 | 91.7 | 98.5 | 98.6 | 85.7 | 95.9 | 96.9 | 94.9 | 59.0 | 93.5 |

PSE = methyl pentenate
*comparative examples using comparative catalysts

We claim:

1. A process for preparing an alkenecarboxylic acid ester of the formula I $$H_2C=C-(CHR_2)_n-COOR_1 \quad\quad I$$
$$\quad\quad |$$
$$\quad\quad R_2$$

where $R_1$ is alkyl of 1 to 6 carbon atoms, $R_2$ is hydrogen or alkyl of 1 to 4 carbon atoms, the substituents being identical or different, and n is 1, 2 or 3, which comprises: reacting a lactone of the formula II

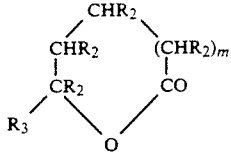

where $R_2$ has the same meanings as in formula I, $R_3$ is hydrogen or methyl and m is 0, 1 or 2, with the proviso that n and m differ by 1 when $R_3$ is hydrogen and by 2 when $R_3$ is methyl, with an alkanol of 1 to 6 carbon atoms at from 50° to 450° C. in the presence of an acidic zeolite.

2. A process as defined in claim 1, wherein the lactone of the formula II is caprolactone.

3. A process as defined in claim 1, wherein the lactone of the formula II is delta-valerolactone or 6-methylvalerolactone.

4. A process as defined in claim 1, wherein the lactone of the formula II is butyrolactone or 5-methylbutyrolactone.

5. A process as defined in claim 1, wherein the catalyst used is a zeolite having a pentasil structure.

6. A process as defined in claim 1, wherein the catalyst used is a borosilicate zeolite, iron silicate zeolite or alumino-silicate zeolite, in each case having a pentasil structure.

7. A process as defined in claim 1, wherein the catalyst used is an aluminosilicate zeolite having a faujasite structure.

8. A process as defined in claim 1, wherein the catalyst used is a zeolite doped with an alkali metal, an alkaline earth metal, a transition metal or a rare earth.

9. A process as defined in claim 1, wherein a molar ratio of lactone of the formula II:alkanol of from 1:0.5 to 1:10 is maintained.

10. A process as defined in claim 1, wherein the reaction is carried out in the gas phase.

* * * * *

UNITED STATES PATENT AND TRADEMARK OFFICE
CERTIFICATE OF CORRECTION

PATENT NO. : 5,144,061

DATED : September 1, 1992

INVENTOR(S) : HOELDERICH et al.

It is certified that error appears in the above-identified patent and that said Letters Patent is hereby corrected as shown below:

ABSTRACT

Alkenecarboxylic esters of the formula I

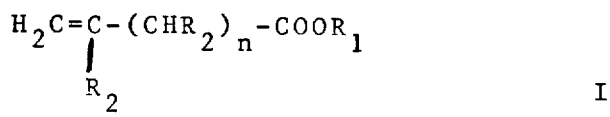

where $R^1$ is alkyl of 1 to 6 carbon atoms, $R_2$ is hydrogen or alkyl of 1 to 4 carbon stoms, the substituents being identical or different, and n is 1, 2 or 3 are prepared by reacting lactones of the formula II

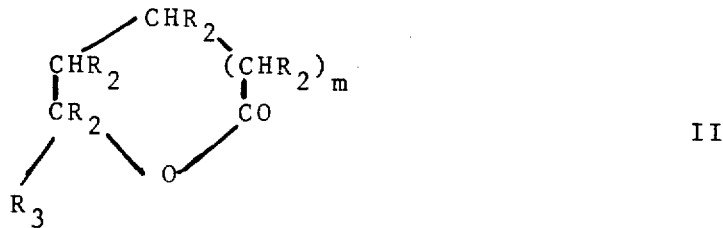

UNITED STATES PATENT AND TRADEMARK OFFICE
CERTIFICATE OF CORRECTION

PATENT NO.  : 5,144,061
DATED       : September 1, 1992
INVENTOR(S) : Hoelderich, et al.

It is certified that error appears in the above-indentified patent and that said Letters Patent is hereby corrected as shown below:

where $R^2$ has the same meanings as in the formula I, $R_3$ is hydrogen or methyl and m is 0, 1 or 2, with the proviso that n and m differ by 1 when $R_3$ is hydrogen and by 2 when $R_3$ is methyl, with alkanols having 1 to 6 carbon atoms at from 50 to 450°C in the presence of zeolites and/or phosphates as catalysts.

Signed and Sealed this

Twenty-eighth Day of September, 1993

Attest:

BRUCE LEHMAN

*Attesting Officer*    *Commissioner of Patents and Trademarks*